United States Patent [19]

Sakai

[11] Patent Number: 4,563,179
[45] Date of Patent: Jan. 7, 1986

[54] BLOCKING CONDITION DETECTION DEVICE IN A FLUID INJECTION SYSTEM

[75] Inventor: Eiichi Sakai, Nara, Japan

[73] Assignee: Sharp Kabushiki Kaisha, Osaka, Japan

[21] Appl. No.: 489,290

[22] Filed: Apr. 28, 1983

[30] Foreign Application Priority Data

Apr. 28, 1982 [JP] Japan .............................. 57-62309[U]
Oct. 20, 1982 [JP] Japan ............................ 57-159519[U]
Jan. 28, 1983 [JP] Japan ............................. 58-12544[U]

[51] Int. Cl.$^4$ .............................................. A61M 5/00
[52] U.S. Cl. ........................... 604/244; 128/DIG. 13; 200/81 R; 200/81.9 M; 200/83 J; 417/38; 604/67; 604/153
[58] Field of Search .............................. 604/50, 65–67, 604/118, 122, 123, 153, 244; 128/DIG. 12, DIG. 13; 200/81 R, 81.9 R, 81.9 M, 82 E, 83 L, 83 J; 417/38

[56] References Cited

U.S. PATENT DOCUMENTS

| | | | |
|---|---|---|---|
| 4,194,974 | 3/1980 | Jonsson | 604/118 X |
| 4,212,591 | 7/1980 | Lamontagne et al. | 417/38 |
| 4,277,227 | 7/1981 | Jenkins | 604/118 X |
| 4,369,780 | 1/1983 | Sakai | 604/123 |
| 4,394,862 | 7/1983 | Shim | 604/67 |
| 4,460,355 | 7/1984 | Layman | 604/118 |

*Primary Examiner*—Dalton L. Truluck
*Attorney, Agent, or Firm*—Birch, Stewart, Kolasch & Birch

[57] ABSTRACT

A medical fluid injection system comprises a flexible conduit, a supply device, a movable element, and a blocking condition detection device. The supply device supplies a pressurized medical fluid through the flexible conduit. The movable element is moved for forcing the flexible conduit in a stressing direction to cause creep in the flexible conduit. The blocking condition detection device detects whether or not the flexible conduit is forced in an anti-stressing direction opposed to the stressing direction. In a specific form of the present invention, a monitor may be provided for monitoring whether the movable element is exactly moved or not.

8 Claims, 17 Drawing Figures

BLOCKING CONDITION DETECTION DEVICE IN A FLUID INJECTION SYSTEM

BACKGROUND OF THE INVENTION

The present invention relates to a fluid injection system and, more particularly, to a blocking condition detection device for a fluid injection system, including a medical system.

A conventional blocking condition detection device for a fluid injection system is disclosed in U.S. Pat. No. 4,369,780, issued Jan. 25, 1983, entitled "BLOCKING CONDITION DETECTION DEVICE IN A MEDICAL FLUID INJECTION SYSTEM", granted to the same applicant. The essence of this patent is as follows:

A medical fluid injection system includes a flexible conduit and a rotor for supplying a pressurized medical fluid to the human body through the flexible conduit. A blocking condition detection unit is provided for detecting an abnormal blocking condition of the flexible conduit. The blocking condition detection unit includes a supporting member for supporting the flexible conduit in a manner that the section of the flexible conduit is forced to show a rectangular configuration. A rod is slidably disposed through the supporting member so that one end of the rod makes contact with the flexible conduit. When an abnormal blocking condition occurs in the flexible conduit, the flexible conduit held by the supporting member expands to depress and shift the rod. The created movement of the rod is detected by a microswitch, whereby the rotation of the rotor is interrupted.

The system of this patent shows a high degree of reliability. The disclosure of this patent is incorporated herein by reference.

As another aspect of a blocking condition detection device for a fluid injection system, attention can be directed to the positive usage of the creep feature of the flexible conduit to detect a small fluid-blocking pressure, in which the diameter of the flexible conduit can change.

SUMMARY OF THE INVENTION

Accordingly, it is an object of the present invention to provide an improved blocking condition detection device in a fluid injection system.

It is another object of the present invention to provide an improved blocking condition detection device in a fluid injection system relying upon the creep feature of a flexible conduit.

It is a further object of the present invention to provide an improved blocking condition detection device in a medical fluid injection system relying upon the creep feature of a flexible conduit.

Yet still a further object of the present invention is to provide an improved blocking detection device in a medical fluid injection system equipped with a monitor for monitoring whether a movable means is exactly operated or not.

Briefly described, in accordance with the present invention, a blocking condition detection device for a fluid injection system applicable to a medical system comprises a movable element, a creep generator, and a detection means. The movable element moves to stress the flexible conduit in a stressing direction to generate creep. The detection means is provided for detecting the condition whereby the flexible conduit and movable element is forced in an anti-stressing direction, opposed to the stressing direction. The detection means thus detects the generation of an abnormal blocking pressure of the flexible conduit.

When no blocking pressure is detected during the condition whereby the flexible conduit is being stressed in the stressing direction, normal operation is maintained. When the flexible conduit is blocked the blocking pressure is detected by the detection means which detects the condition whereby the flexible conduit is stressed in the anti-stressing direction.

In a preferred form of the present invention, a monitor is provided for monitoring whether the movable element is moved or not.

BRIEF DESCRIPTION OF THE DRAWINGS

The present invention will become more fully understood from the detailed description given hereinbelow and accompanying drawings which are given by way of illustration only, and thus are not limitative of the present invention and wherein.

DESCRIPTION OF THE INVENTION

Figure 1:
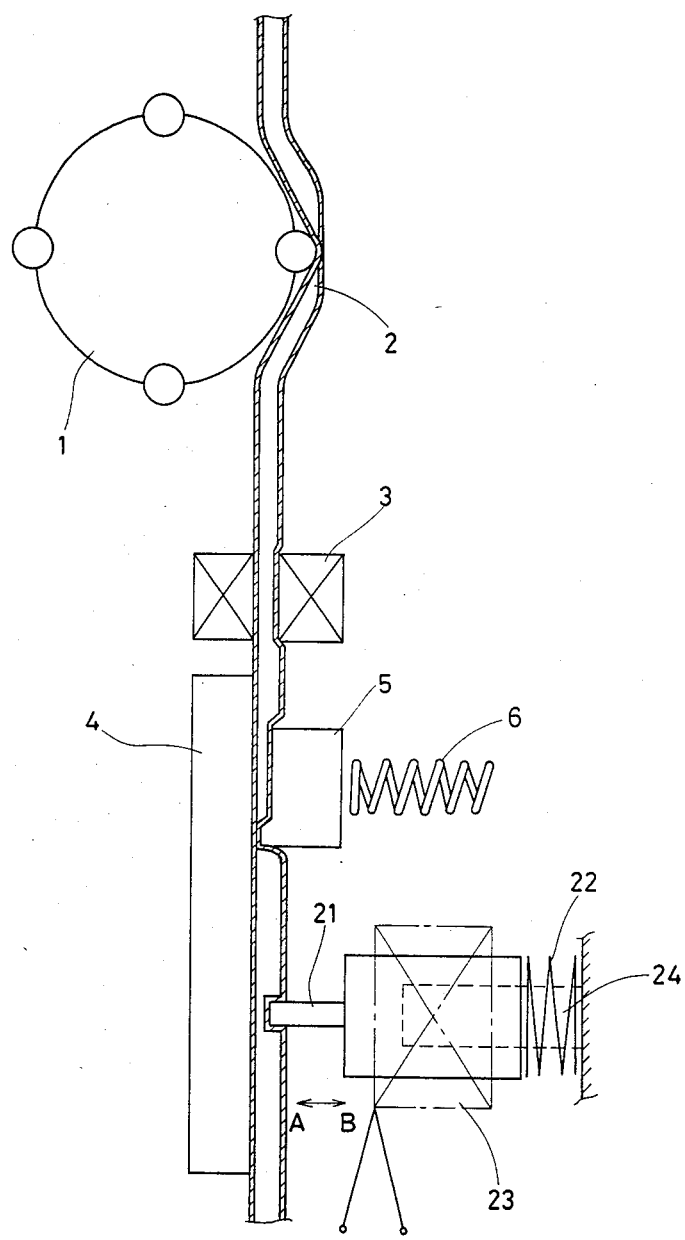
FIG. 1 shows a sectional view of a medical fluid injection system according to a specific embodiment of the present invention.

FIG. 1 shows a blocking condition detection device for a fluid injection system of a medical system. The system of FIG. 1 comprises a rotor 1, a flexible conduit 2 such as a vinyl tube, a ultrasonic air sensor 3, a support plate 4, a movable clamp 5, a first spring 6, a movable element 21, a second spring 22, a coil 23, and a core 24.

A medical fluid is supplied downward to the human body at a predetermined flow rate by the rotation of the rotor 1 through the conduit 2. The ultrasonic air sensor 3 is provided for detecting air bubbles present in medical fluid. If the sensor 3 detects that the air bubbles are mixed within the medical fluid, the rotation of the rotor 1 is interrupted to terminate the supply of the fluid.

The support plate 4, the movable clamp 5, and the spring 6 serve to prevent the gravity flow of the medical fluid when the rotor 1 is not rotated. That is because it is not desirable for the medical fluid contained within the conduit 2 to continue to flow to the human body, due to gravity, when the rotor 1 is not rotating.

While the rotor 1 stops, the clamp 5 is pressed toward the conduit 2 with the help of the spring 6 to block the conduit 2. When the rotor 1 is rotated to cause the fluid to flow under pressure, the pressure of the fluid causes the clamp 5 to move backward to release the blockage of the conduit 2.

The movable element 21 is provided for moving in a stressing direction A toward the conduit 2 and an anti-stressing direction B away from the conduit 2. The second spring 22 forces the movable element 21 in the stressing direction A to generate creep in the conduit 2. The spring 22 forms the creep generator according to the present invention. The spring 22 stresses the conduit 2 so that the conduit is incompletely blocked and, in addition, creep is generated in the conduit 2. The creep as used herein means a time-dependent strain of the solid, namely, the conduit 2, caused by a constant stress.

The coil 23 and the core 24 in combination serve to detect the moving direction of the movable element 21.

The coil 23 forms an LC resonance circuit. The movement of the element 21 is detected by detecting the change of the resonance frequency. When the element 21 moves in the stressing direction A, the inductance of the coil 23 decreases to make the resonance frequency high. When the element 21 moves in the anti-stressing direction B, the conductance of the coil 23 increases to make the resonance frequency low.

FIGS. 2(A) to 2(E) show operations of the system of FIG. 1.

Figure 2A:
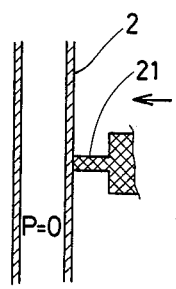
FIGS. 2(A) to 2(E) show operations of the essential parts of the system as shown in FIG. 1.
Figure 2B:
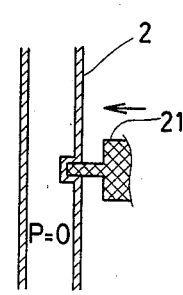

FIGS. 2(A) and 2(B): The peripheral surface of the conduit 2 is stressed by the element 21 forced by the spring 22. Depending upon the characteristics of the conduit 2, creep of the conduit 2 is generated as shown in these drawings. As time lapses, the conduit 2 is blocked in the stressing direction.

Figure 2C:
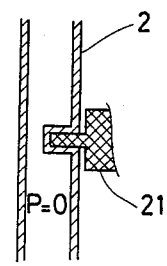

FIG. 2(C): When a predetermined time lapses, the conduit 2 is not blocked anymore according to the stress limitation of the spring 22.

Figure 2D:
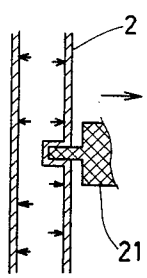
Figure 2E:
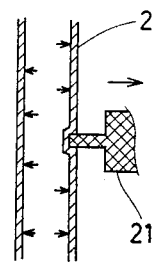

FIGS. 2(D) and 2(E): When a blocking pressure is generated within the conduit 2, the element 21 is moved in the anti-stressing direction B against the force of the spring 22. This blocking condition is detected by detecting the movement direction of the element 21.

Thus, while the conduit 2 is normal and not blocked, the element 21 is moved in the stressing direction A as shown in FIGS. 2(A) and 2(B). The element 21 stops after the creep is generated in the conduit 2 as shown in FIG. 2(C). At this time, the detection means for detecting the decrease of the resonance frequency f is not operated to detect that the element 21 is moved in the anti-stressing direction B.

As FIGS. 2(D) and 2(E) show, when the conduit 2 is blocked to some degree, the peripheral surface of the conduit 2 is expanded in the anti-stressing direction B due to the generation of the abnormal blocking stress, to thereby decrease the creep degree. As a result, the element 21 is moved in the anti-stressing direction B. The detection means is operated to detect the abnormal blocking conditions of the conduit 2. Responsive to the detection output, the rotor 1 stops.

Attention is directed to another preferred form of the present invention where a monitor element is provided for monitoring that the movable element for detecting the abnormal blocking conditions of the conduit 2 is exactly moved.

Figure 3:
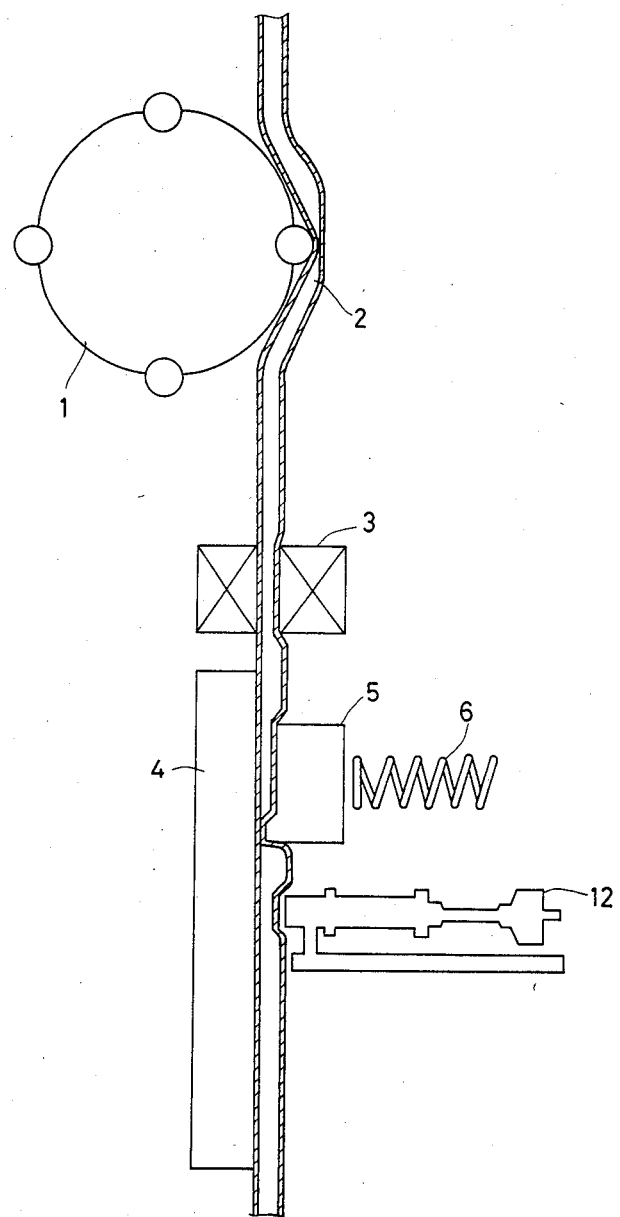
FIG. 3 shows a sectional view of a medical fluid injection system according to another preferred embodiment of the present invention.

FIG. 3 shows a medical fluid injection system according to another preferred form of the present invention. Like elements corresponding those of FIG. 1 are represented by like numerals.

In terms of the above preferred form of the present invention as shown in FIG. 1, it may be difficult to exactly detect the small change of the inner pressure of the conduit 2. Further it may be possible that the element 21 cannot be moved by the intrusion of a foreign body into the engagement between the core 24 and the element 21. In such a case, even when the inner pressure of the conduit 2 is remarkably changed, this change cannot be detected.

To overcome this condition, according to another preferred form of the present invention, the blocking condition detection device 12 comprises a monitor for monitoring the operation of the movable element for detecting the abnormal blocking conditions of the conduit 2.

Figure 4:
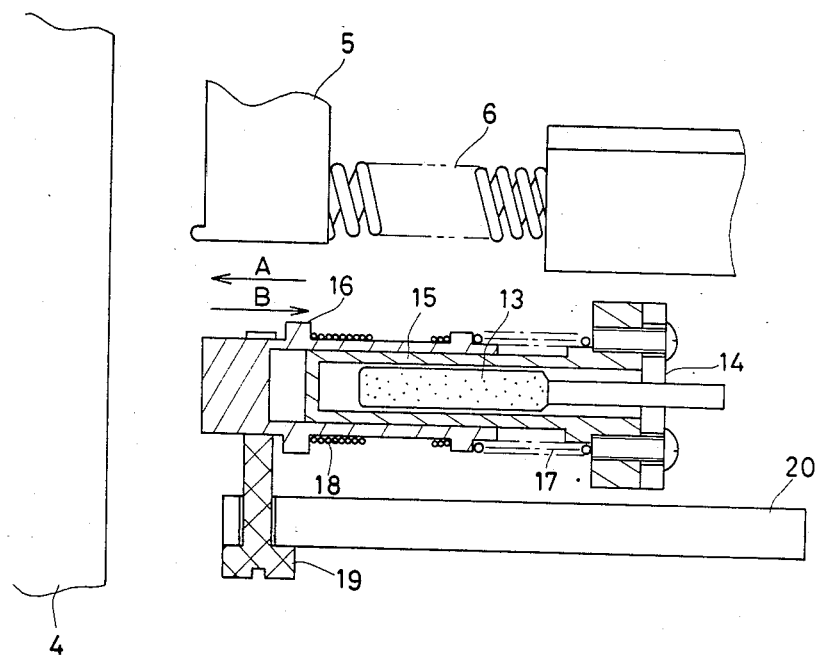
FIG. 4 shows a sectional view of a blocking condition detection means adapted to the system of FIG. 3.

FIG. 4 shows a sectional view of the blocking condition detection device 12. The blocking condition detection device 12 comprises a core 13, a core fixing plate 14, a shaft 15, a rod 16, a compressed-coil spring 17, a coil 18, a pin 19, and a slider 20.

The core 13 and the shaft 15 are both fixed to the plate 14. The shaft 15 contains the core 13. The shaft 15 is engaged with the rod 16. Therefore, the rod 16 can be moved relative to the core 13, so that the rod 16 can be moved in the direction A.

Since the coil 18 is disposed around the rod 16, the magnetic flux formed by the coil 18 can be changed in response to the shift of the rod 16 in the direction A. The rod 16 can also be moved in the direction B, so that the magnetic flux of the coil 18 can be changed.

According to the above engagement, when the rod 16 is moved in the direction A, the inductance L of the coil 18 decreases, so that the resonance frequency f becomes high. When the rod 16 is moved in the direction B, the inductance L of the coil 18 increases, so that the resonance frequency f becomes low.

The rod 16 is stressed normally in the direction A by the compressed-coil spring 17.

Figure 5:
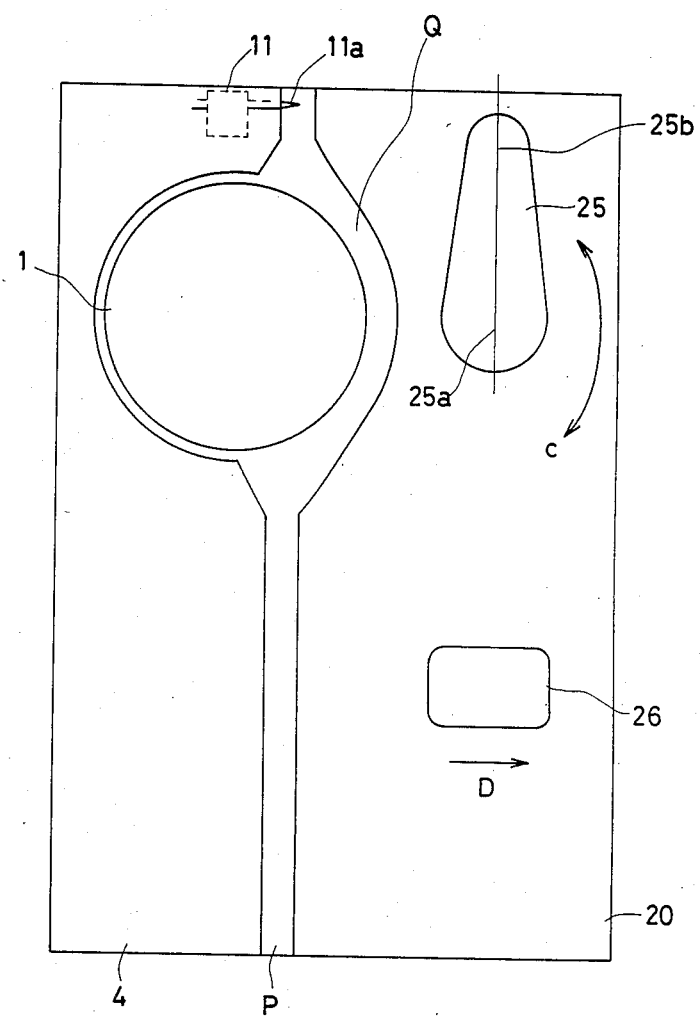
FIGS. 5 and 6 show operations of the blocking condition detection means of FIG. 4.
Figure 6:
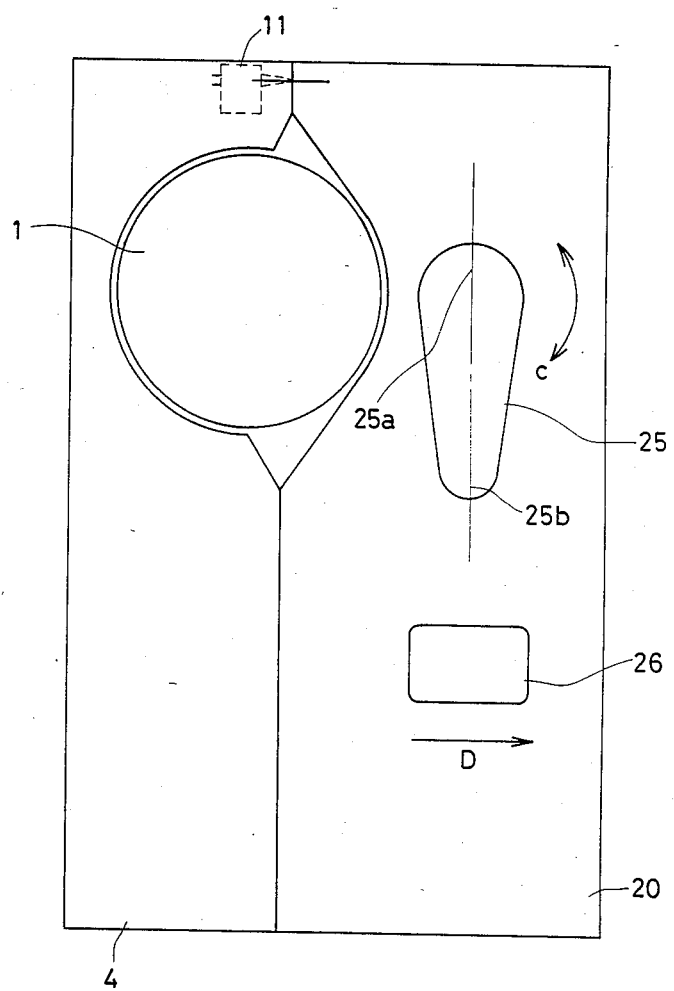

The marble element is monitored whether the shaft 15 and the rod 16 are exactly engaged, as shown in FIGS. 5 and 6 and described below:

As parts of the blocking condition detection means 12, the shaft 15 and the rod 16 must be moved smoothly. If the blocking condition detection means 12 is not operated smoothly, no medical fluid must be injected.

As described above, the medical fluid flows at a constant rate according to the rotation of the rotor 1. As FIG. 5 shows, the fluid injection system initially provides a parallel space P between the plate 4 and the slider 20.

In FIG. 5, a knob 25 is actuated for opening and closing the slider 20. The knob 25 has a point 25a around which a head 25b of the knob 25 is rotated in a direction C. The head 25b is positioned at the upper position of the point 25a as shown in FIG. 5. The head 25b is manually rotated in the direction C until the head 25b is positioned at the lower position of the point 25a as shown in FIG. 6, wherein the edge of the slider 20 becomes in contact with the plate 4 eliminating the formation of the space P. As FIG. 5 shows, the roll 1 and the slide 20 are separated by a portion Q for containing the conduit 2.

In FIGS. 5 and 6, a microswitch 11 with a probe tip 11a is fixed on the plate 4. The tip 11a protrudes in the space P between the plate 4 and the clamp 5.

When the plate 4 and the slider 20 become in contact, the tip 11a becomes in contact with the slider 20, so that the microswitch 11 is switched on.

In FIG. 5, a knob 26 is actuated for opening and closing the clamp 5. When the knob 26 is manually shifted in a direction D, the clamp 5 is opened, in which the conduit 2 is not blocked.

Thus, the conduit 2 is surrounded by the rod 16, the plate 4, and the slider 20. As the knob 25 is rotated, the slider 20 is moved till the stage of FIG. 6 is reached. As the slider 20 is moved, the rod 16 is moved toward the plate 4 until the rod 16 becomes in contact with the conduit 2. The rod 16 is connected with the slider 20 by the pin 19. Since the rod 16 is coupled with the compressed-coil spring 17, the rod 16 tends to be moved toward the plate 4 along the direction A of FIG. 4. Hence, the rod 16 blocks the conduit 2 for a predetermined time. The blocking operation of the rod 16 upon the conduit 2 is terminated because the stress of the rod 16 by the coil spring 17 balances the creep force of the conduit 2.

It may be evident that, if the rod 16 and the shaft 15 are not exactly engaged, the rod 16 cannot go toward the plate 4 even in response to the force of the coil spring 17.

Thus, the blocking condition detection device 12 monitors whether the shaft 15 and the rod 16 are exactly engaged.

Figure 7:
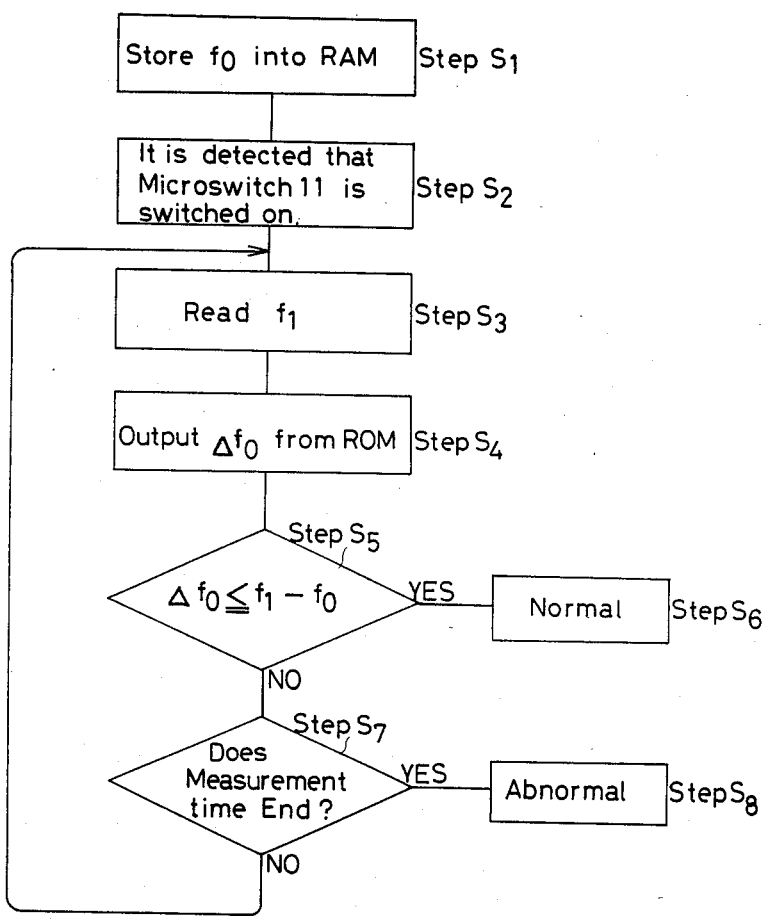
FIG. 7 shows a flow chart of the operation of the system of FIG. 3.

FIG. 7 shows a flow chart of the operation of the blocking condition detection device 12, with monitoring whether the shaft 15 and the rod 16 are exactly engaged.

Step S1: This step is executed to store a resonance frequency f0 into a RAM of a microcomputer. The resonance frequency f0 corresponds to the initial stage of FIG. 5.

Step S2: This step is executed to detect whether the microswitch 11 is turned on at the position of FIG. 6. At this time, the rod 16 is in contact with the conduit 2.

Step S3: This step is executed to read in a resonance frequency f1 corresponding to the position of the rod 16 after a predetermined time lapses after the rod 16 is positioned at the appropriate position by step S2. The predetermined time is counted by a timer of the microcomputer as related to the blocking condition detection device 12.

Step S4: This step is executed to read out a preset resonance frequency delta f0. This preset resonance frequency is stored in a ROM of the microcomputer.

Step S5: This step is executed to compare delta f0 and the difference between f1 and f0.

delta f0 ≦ f1 − f0

Step S6: This step is referred to the movement of the rod 16 from the initial position of FIG. 5 to an appropriate position after a predetermined time lapses after the rod 16 occupies the position of FIG. 6 from the initial position of FIG. 5. At this time, it is determined that the rod 16 and the core 13 are exactly engaged, so that the blocking condition detection means 12 can be operated.

Step S7: This step is executed to repeat the operation of step S3 until a predetermined time lapses after the rod 16 is positioned at an appropriate position, even if the requirement of step S5 is not satisfied. If the requirement of step S5 is not satisfied and a predetermined time lapses after the rod 16 is positioned at an appropriate position, the following step S8 is selected.

Step S8: The selection of this step means that the rod 16 is not moved from the initial position of FIG. 5 to an appropriate position, even when a predetermined time lapses after the rod 16 is moved from the position of FIG. 5 to that of FIG. 6. This means that the rod 16 and the core 13 are abnormally engaged, so that the blocking condition detection device 12 should not be operated. When the coil 18 around the peripheral surface of the rod 16 is cut, the abnormal condition can be detected because the resonance frequency f to be measured varies.

Thus, it is monitored whether the rod 16 and the shaft 15 are exactly engaged. This monitoring operation indicates whether the blocking condition detection means 12 can be correctly operated or not. This assures that the blocking condition detection device 12 which can be correctly operated is actually connected to the medical fluid injection system when assembled.

Figure 8A:
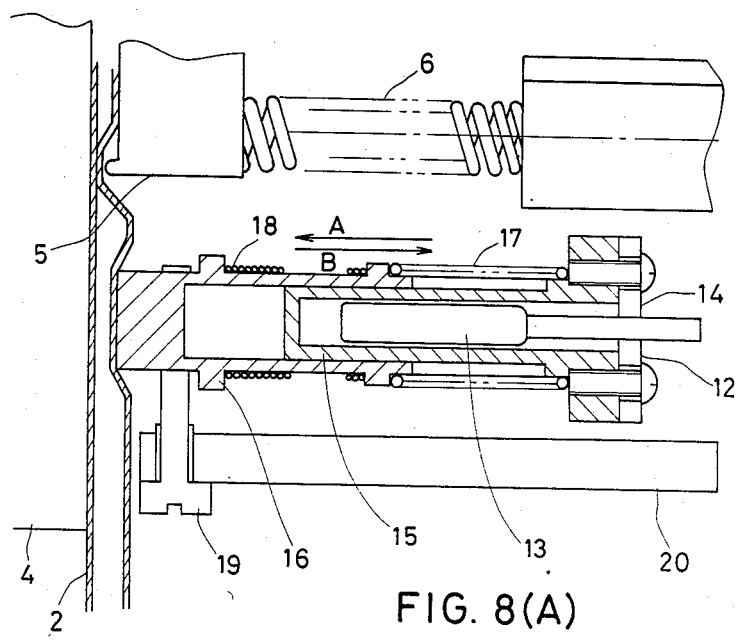
FIGS. 8(A) and 8(B) show sectional views of the system of FIG. 3.
Figure 8B:
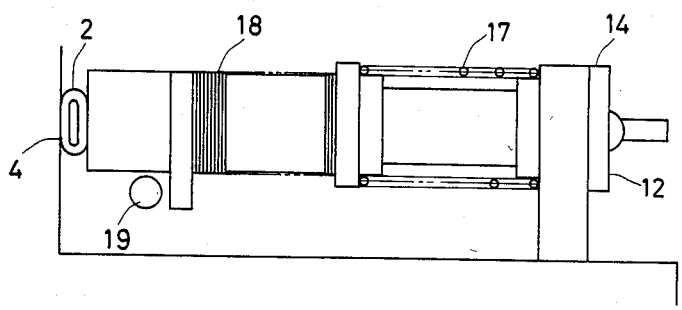

FIGS. 8(A) and 8(B) show a medical fluid injection system to which the correctly-operated blocking condition detection device 12 is connected.

The blocking condition detection device 12 is applied to the medical fluid injection system to inject medical fluid. When the conduit 2 is blocked for some reason, the conduit 2 becomes expanded. Responsive to this expansion, the rod 16 of the blocking condition detection device 12 is moved in the direction B against the force of the coil spring 17. This movement of the rod 16 permits the abnormal blocking condition of the conduit 2 to be detected by detecting the change of the resonance frequency f by the inductance L of the core 13 and the coil 18. The coil 18 is around the rod 16. The core 13 functions as an iron core of the coil 18.

Figure 9:
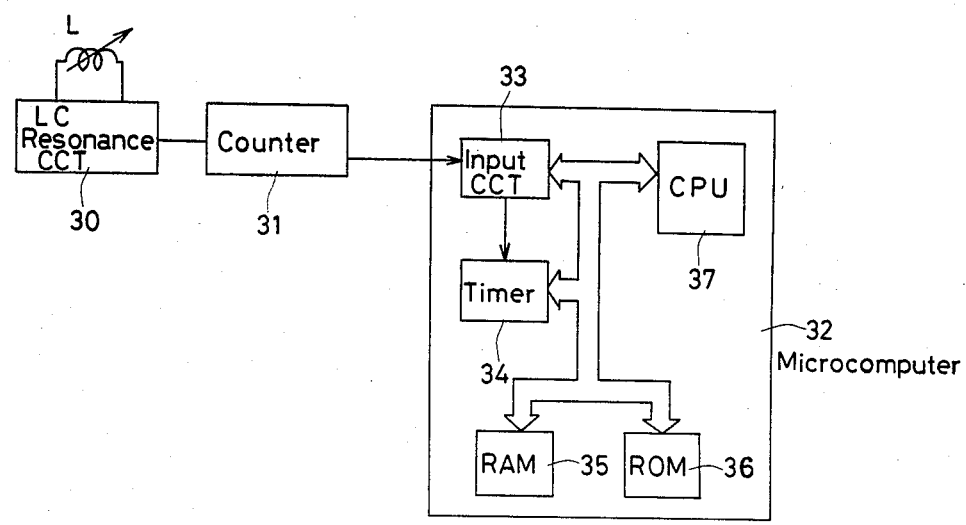
FIG. 9 shows a block diagram of a circuit for the system of FIG. 3.

FIG. 9 shows a block diagram of the microcomputer adaped for the medical fluid injection system of FIG. 8. The microcomputer is operated to detect the blocking condition of the conduit 2.

The electrical circuit of the medical fluid injection system comprises an LC resonance circuit 30, a counter 31, and a microcomputer 32. The microcomputer 32 includes an input circuit 33, a timer 34, a RAM 35, a ROM 36, and a CPU 37.

The LC resonance circuit 30 is provided for converting the position of the rod 16 into the resonance frequency. The resonance circuit 30 is electrically connected to the coil 18. The resonance frequency from the resonance circuit 30 is inputted into the counter 31. The counter 31 counts the resonance frequency and outputs a single pulse by counting $2^n$ (n: a positive integer). The counter 31 is an n-stage ripple carry binary counter.

The counted output from the counter 31 is applied to the input circuit 33. Responsive to the counted output of the counter 31, the timer 34 measures the width of the single pulse. The CPU 37 detects the resonance frequency f by detecting the pulse width and the counted number.

The RAM 35 stores the resonance frequency f0 as stated in step S1. The ROM 36 stores the resonance frequency delta f0 as stated in step S5.

With the help of the microcomputer 32, the change of the resonance frequency f is detected, so that the CPU 37 detects that the conduit 2 is blocked, to thereby stop the fluid injection by stopping the rotor 1.

Figure 10:
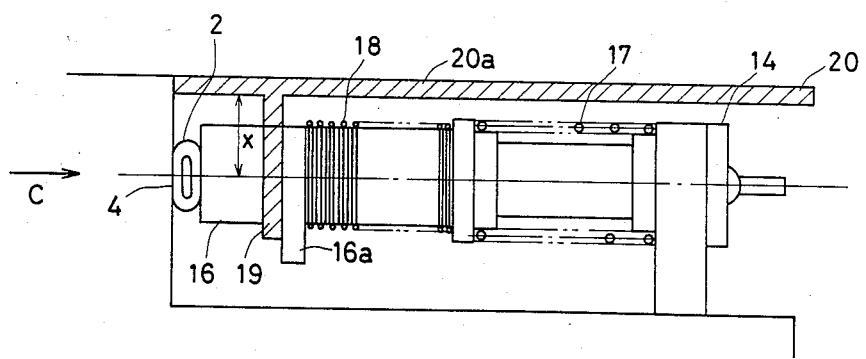
FIG. 10 shows a side view of the stage of FIG. 6.

As described with reference to FIG. 4, when the rod 16 is moved in the direction A, the brim of the rod 16 is engaged with the pin 19 connected to the slider 20, so that the slider 20 is moved in the direction A. FIG. 10 shows a side view of the stage of FIG. 6. FIG. 10 indicates that the slider 20 is moved in the direction A by engaging a brim 16a of the rod 16 and the pin 19.

Figure 11:
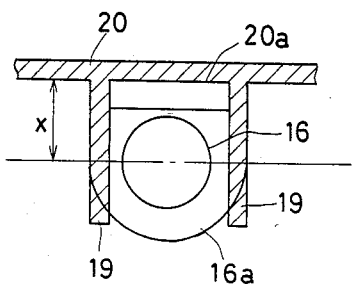
FIG. 11 shows a front view of the view of FIG. 10.

FIG. 11 shows a front view of the stage of FIG. 10, viewed along the direction C of FIG. 10.

With reference to FIGS. 10 and 11, a side 20a of the slider 20 confronts the rod 16. The rod 16 has a circular section and the brim 16a of the rod 16 has a semicircular section. There are provided two pins 19 each corresponding to the left and the right edges of the brim 16a.

As FIG. 11 shows, the brim 16a does not become contact with the side 20a when assembled. The space between the rod 16 and the slider 20 cannot be much large. Strictly speaking, the space between the rod 16 and the slider 20 is represented by a diatance x, in FIGS. 10 and 11, between the center of the rod 16 and the surface of the side 20a.

Therefore, the rod 16 may be rotated around the shaft 15 while being engaged with the shaft 15. In such a case, the rod 16 is rotated, so that the brim 16a is also rotated. At a portion of the brim 16a which has a distance from the center of the rod 16 more than the distance x, the brim 16a becomes contact with the side 20a of the slider 20.

If the rod 16 is contact with the brim 20a, the rod 16 is prevented from being moved and forcing the conduit 2. Such faults may be present in another preferred form of the present invention.

To eliminate this fault, according to a further preferred form of the present invention, the rotation of the rod 16 around the shaft 15 is prevented, so that the normal operation of the rod 16 and the movable element are assured.

Figure 12:
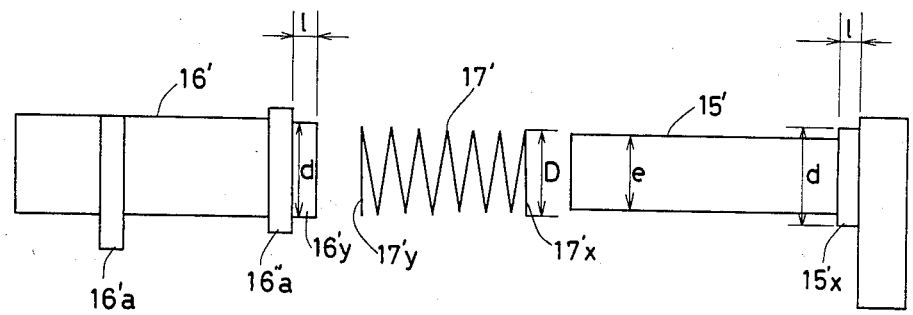
FIG. 12 shows a rod movable section adapted for the system of FIG. 3.

FIG. 12 shows a rod portion suitable for a medical fluid injection system according to a further preferred form of the present invention.

The rod portion of FIG. 12 comprises a shaft 15', a rod 16', and a compressed-coil spring 17'. The rod 16' has a brim 16'a.

According to a further form of the present invention, the following relation is satisfied:

$$d > D > e$$

wherein
e: the diameter of the shaft 15'
D: the diameter of the compressed-coil spring 17'
d: the diameter of an end 16'y of the rod 16' to which the shaft 15' is inserted.

At the other end of the shaft 15', a root 15'x has a diameter of d similar to that of the end 16'y. The end 16'y is separated from the rod 16' by a rod brim 16"a.

When the parts are assembled to form the rod structure, the following construction steps are performed:

(1) The end 17'y of the coil spring 17' is expanded to grasp the end 16'y of the rod 16'.

(2) The shaft 15' is surrounded by a blank opening of the coil spring 17'. One end of the coil spring 17' is connected to the rod 16'.

(3) The tip of the shaft 15' and its neighbors are inserted into the shaft rod 16'.

(4) The end 17'x of the coil spring 17' reaching the root 15'x of the shaft 15' by the insertion is expanded to grasp the root 15'x of the shaft 15'.

Thus, the rod structure comprises the shaft 15', the rod 16' connected to the shaft 15', and the coil spring 17'. The coil spring 17' is positioned at the unengaged portion between the shaft 15' and the rod 16'. The ends of the shaft 17' are grasped by the shaft 15' and the rod 16'.

The ends 17'x and 17'y of the coil spring 17' are expanded, so that these ends force the end 16'y of the rod 16' and the root 15'x of the shaft 15' to be back toward the original forms.

Once the rod structure is constructed as above, the rod 16' and the shaft 15' are mechanically combined by the coil spring 17', so that the rod 16' cannot be rotated around the shaft 15'. After the rod slidable portion is set as shown in FIG. 11, it can be eliminated that the brim 16'a of the rod 16' becomes contact with the slider 20 due to the rotation of the rod 16'.

The length of each of the root 15' of the shaft 15' and the end 16'y of the rod 16' is indicated by l of FIG. 12. The length l is enough to grasp the ends 17'x and 17'y of the coil spring 17'. It is unnecessary that the length l is very long, because, otherwise, the friction between the coil spring 17' and the shaft 15' becomes too great, so that the coil spring 17' is of no use.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A fluid injection system comprising:
   a flexible conduit;
   supply means for supplying a pressurized fluid through said flexible conduit;
   movable means to force the flexible conduit in a stressing direction said movable means including a spring means and a movable element wherein said spring means provides a stress via said movable element to cause creep in said flexible conduit; and
   blocking condition detection means comprising a coil means and core means to form a resonance circuit for detecting whether or not the flexible conduit is forced in an anti-stressing direction opposed to said stressing direction thereby indicating that a blocking condition has developed in said flexible conduit, wherein movement of said movable means is detected in terms of the change of a resonance frequency, said resonance frequency increasing when the movable means stresses the flexible conduit to create a creep condition in said conduit and said resonance frequency decreasing when the movable means is forced in said anti-stressing direction separated from the flexible conduit.

2. The system of claim 1, further including a monitor means for monitoring movement by said movable element.

3. The system of claim 2, wherein said monitor means comprises spring means for supplying a force to the movable element to balance creep force of the flexible conduit.

4. The system of claim 2, wherein said detection means further comprises a counter and a microcomputer.

5. The system of claim 1, wherein said movable element comprises a rod means further, and the blocking condition detection means comprises
   a shaft means which contains said core and is engaged with said rod means such that said rod means can move relative to said shaft means, and
   a spring means disposed at unengaged portions of the rod means and shaft means between the shaft means and the rod means, so that respective ends of the spring means are grasped by each of the shaft means and the rod means.

6. A detection system for detecting a blocking condition in a flexible conduit through which a pressurized fluid is supplied, said detection system comprising:
a movable means to force said flexible conduit in a stressing direction, said movable means including a spring means and a movable element wherein said spring means provides a stress via said movable element to cause creep in said flexible conduit; and blocking condition detection means comprising a coil means and core means to form a resonance circuit for detecting whether or not said flexible conduit is forced in an anti-stressing direction opposed to said stressing direction, thereby indicating that a blocking condition has developed in said flexible conduit.

7. The detection system of claim 6, wherein said detection means further comprises a resonance circuit, a counter and a microcomputer.

8. The detection system of claim 6, wherein said movable element comprises a rod means, said detection means comprises a shaft means which contains said core and is engaged with said rod means such that said rod means can move relative to said shaft means and a spring means disposed at unengaged portions of the rod means and shaft means between the shaft means and the rod means, so that respective ends of the spring means are grasped by each of the shaft means and the rod means.

* * * * *